United States Patent
Stork et al.

(10) Patent No.: US 9,695,142 B2
(45) Date of Patent: *Jul. 4, 2017

(54) METHOD FOR PRODUCING 2-SUBSTITUTED 4-HYDROXY-4-METHYL-TETRAHYDROPYRANS, SAID METHOD USING RECYCLING

(71) Applicant: BASF SE, Ludwigshafen (DE)

(72) Inventors: Timon Stork, Mannheim (DE); Karl Beck, Östringen (DE); Gabriele Gralla, Mannheim (DE); Oliver Bey, Niederkirchen (DE); Klaus Ebel, Heddesheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/787,312

(22) PCT Filed: Apr. 28, 2014

(86) PCT No.: PCT/EP2014/058536
§ 371 (c)(1),
(2) Date: Oct. 27, 2015

(87) PCT Pub. No.: WO2014/177484
PCT Pub. Date: Nov. 6, 2014

(65) Prior Publication Data
US 2016/0060238 A1    Mar. 3, 2016

(30) Foreign Application Priority Data

Apr. 29, 2013  (EP) .................................. 13165778

(51) Int. Cl.
*C07D 321/00* (2006.01)
*C07D 315/00* (2006.01)
*C07D 309/10* (2006.01)

(52) U.S. Cl.
CPC .................................. *C07D 309/10* (2013.01)

(58) Field of Classification Search
CPC .................................................... C07D 309/10
(Continued)

(56) References Cited

U.S. PATENT DOCUMENTS 2,471,134  A    5/1949  Wright
8,618,315  B2   12/2013 Gralla et al.
(Continued)

FOREIGN PATENT DOCUMENTS

EP    0 122 367 A2    10/1984
EP    1493737 A1      1/2005
(Continued)

OTHER PUBLICATIONS

Gevorkyan A. A. et al., "Mechanism of Cycloalkylation of Allylcarbinols with Aldehydes and Ketones", *Chemistry of Heterocyclic Compounds*, No. 12, pp. 1240-1242, (Jan. 1, 1982); XP002597060.
(Continued)

*Primary Examiner* — T. Victor Oh
(74) *Attorney, Agent, or Firm* — Drinker Biddle & Reath LLP

(57) ABSTRACT

The present invention relates to a process for the preparation of 2-substituted 4-hydroxy-4-methyltetrahydropyrans.

19 Claims, 1 Drawing Sheet

(58) Field of Classification Search
USPC .................................................. 549/200, 416
See application file for complete search history.

(56) References Cited

U.S. PATENT DOCUMENTS

| | | | |
|---|---|---|---|
| 9,056,812 B2 | 6/2015 | Schuch et al. | |
| 9,073,826 B2 | 7/2015 | Ebel et al. | |
| 9,139,549 B2 | 9/2015 | Stork et al. | |
| 2011/0295024 A1 | 12/2011 | Gralla et al. | |
| 2014/0163117 A1 | 6/2014 | Rudenauer et al. | |
| 2014/0200351 A1 | 7/2014 | Bey et al. | |
| 2014/0200369 A1 | 7/2014 | Bey et al. | |
| 2014/0200370 A1 | 7/2014 | Bey et al. | |
| 2016/0068500 A1* | 3/2016 | Stork .................. | C07D 309/10 549/423 |

FOREIGN PATENT DOCUMENTS

| | | |
|---|---|---|
| EP | 1516879 A1 | 3/2005 |
| EP | 12188518.0 | 10/2012 |
| WO | WO-2010133473 A1 | 11/2010 |
| WO | WO2011/154330 | * 12/2011 |
| WO | WO-2011154330 A1 | 12/2011 |
| WO | WO-2014060345 A1 | 4/2014 |

OTHER PUBLICATIONS

Macedo A. et al, "Solvent-free Catalysed Synthesis of Tetrahydropyran Odorants: the Role of SiO2 p-TSA Catalyst on the Prins-Cyclization Reaction", *Journal of the BR Chemical Society*, vol. 21, No. 8, pp. 1563-1571 (May 4, 2010); XP002661261.
International Preliminary Report on Patentability for PCT/EP2014/058536 mailed Nov. 12, 2015.
U.S. Appl. No. 14/787,285, filed Oct. 27, 2015, Stork.
International Search Report for PCT/EP2014/058536 mailed Jun. 24, 2014.

\* cited by examiner

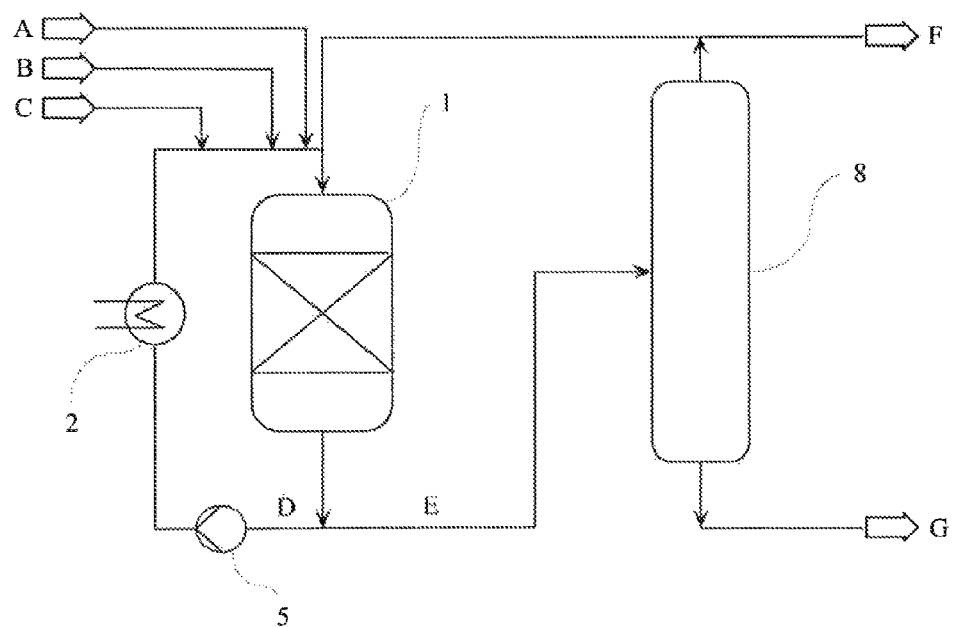

METHOD FOR PRODUCING 2-SUBSTITUTED 4-HYDROXY-4-METHYL-TETRAHYDROPYRANS, SAID METHOD USING RECYCLING

CROSS-REFERENCE TO RELATED APPLICATIONS

This application is a national stage application (under 35 U.S.C. §371) of PCT/EP2014/058536, filed Apr. 28, 2014, which claims benefit of European Application No. 13165778.5, filed Apr. 29, 2013, both applications of which are incorporated herein by reference in their entirety.

BACKGROUND OF THE INVENTION

The present invention relates to a process for the preparation of 2-substituted 4-hydroxy-4-methyltetrahydropyrans.

PRIOR ART

2-Substituted 4-hydroxy-4-methyltetrahydropyrans are valuable compounds for use as aroma chemicals. Thus, for example, the cis/trans diastereomer mixture of 2-(2-methylpropyl)-4-hydroxy-4-methyltetrahydropyran

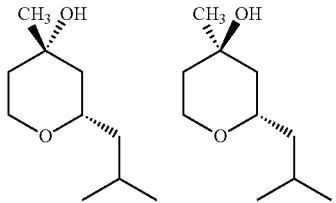

is characterized by a pleasant lily of the valley scent and is especially suitable for use as an aroma chemical, e.g. for producing fragrance compositions.

EP 1 493 737 A1 discloses a process for the preparation of mixtures of ethylenically unsaturated 4-methyl- or 4-methylenepyrans and the corresponding 4-hydroxypyrans by reaction of the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydration of said mixtures to give the desired ethylenically unsaturated pyrans. Suitable catalysts specified for the first reaction step are mineral acids such as hydrochloric acid or sulfuric acid, but preferably methanesulfonic acid or p-toluenesulfonic acid.

EP 1 516 879 A1 discloses a process for the preparation of ethylenically unsaturated 4-methyl- and 4-methylenepyrans by reaction of a corresponding aldehyde with isoprenol under dehydrating conditions, where the amount of water in the reactor is up to 0.25% by weight, while the conversion of the starting compound used in deficit is less than 50%. Catalysts that are specified as being suitable for this purpose are likewise mineral acids such as hydrochloric acid or sulfuric acid, but preferably methanesulfonic acid or p-toluenesulfonic acid.

WO 2010/133473 describes a process for the preparation of 2-substituted 4-hydroxy-4-methyltetrahydropyrans of the formula (I)

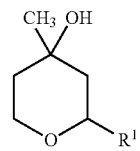

(I)

where the radical $R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms, in which isoprenol (3-methylbut-3-en-1-ol) is reacted with an aldehyde of the formula $R^1$—CHO, where the reaction is carried out in the presence of water and in the presence of a strongly acidic cation exchanger.

WO 2011/154330 describes a process comparable to WO 2010/133473, where the resulting reaction mixture is carried out a distillative work-up in a dividing-wall column or in two thermally coupled distillation columns.

The unpublished European patent application 12188518.0 describes a process for the preparation of 2-substituted 4-hydroxy-4-methyltetrahydropyrans of the general formula (I) and of 2-substituted 4-methyltetrahydropyrans of the general formula (II)

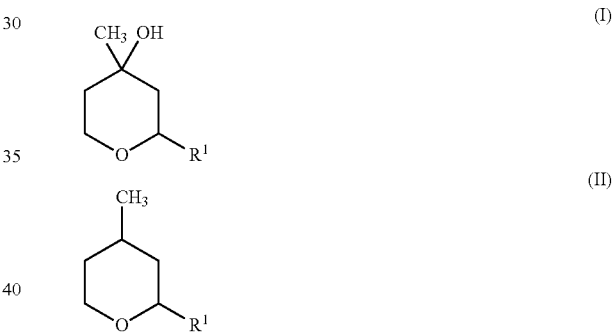

in which
$R^1$ is a straight-chain or branched $C_1$-$C_{12}$-alkyl, straight-chain or branched $C_2$-$C_{12}$-alkenyl, unsubstituted or $C_1$-$C_{12}$-alkyl and/or $C_1$-$C_{12}$-alkoxy-substituted cycloalkyl having in total 3 to 20 carbon atoms or unsubstituted or $C_1$-$C_{12}$-alkyl and/or $C_1$-$C_{12}$-alkoxy substituted aryl having in total 6 to 20 carbon atoms,
in which
a) 3-Methylbut-3-en-1-ol of the formula (III)

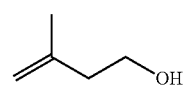

(III)

is reacted with an aldehyde of the formula (IV)

$R^1$—CHO (IV)

where $R^1$ in the formula (IV) has the meaning given above,
in the presence of an acidic catalyst, giving a reaction mixture which comprises at least one 2-substituted 4-hydroxy-4-methyltetrahydropyran of the general formula (I), at least one of the compounds (V.1), (V.2) or (V.3) and at least one dioxane compound (VI)

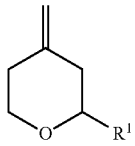
(V.1)

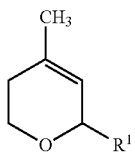
(V.2)

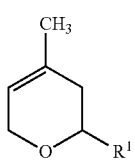
(V.3)

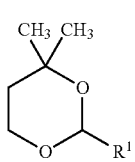
(VI)

where $R^1$ in the formula (VI) has the meaning given above, b) the reaction product from step a) is subjected to a separation, giving a fraction enriched in 2-substituted 4-hydroxy-4-methyltetrahydropyrans of the general formula (I) and a fraction which comprises at least one of the compounds (V.1), (V.2) or (V.3) and at least one dioxane compound (VI), c) the fraction which comprises at least one of the compounds ((1), (V.2) or (V.3) and at least one dioxane compound (VI) is subjected to a hydrogenation, d) a fraction enriched in 2-substituted 4-methyltetrahydropyrans (II) and a fraction enriched in at least one dioxane compound (VI) are isolated from the hydrogenation product obtained in step c).

SUMMARY OF THE INVENTION

The object of the present invention is to provide an improved process for the preparation of 2-substituted 4-hydroxy-4-methyltetrahydropyrans which permits an effective preparation on an industrial scale with the lowest possible formation of undesired byproducts requiring disposal.

Surprisingly, it has now been found that this object is achieved by a procedure using at least one reactor operated in loop mode with downstream separating column. Specifically, it is a continuous process.

The invention provides a process for the preparation of 2-substituted 4-hydroxy-4-methyltetrahydropyrans of the general formula (I)

(I)

in which
$R^1$ is a straight-chain or branched $C_1$-$C_{12}$-alkyl, straight-chain or branched $C_2$-$C_{12}$-alkenyl unsubstituted or $C_1$-$C_{12}$-alkyl- and/or $C_1$-$C_{12}$-alkoxy substituted cycloalkyl having in total 3 to 20 carbon atoms or unsubstituted or $C_1$-$C_{12}$-alkyl and/or $C_1$-$C_{12}$-alkoxy substituted aryl having in total 6 to 20 carbon atoms, comprising a reaction of 3-methylbut-3-en-1-ol of the formula (III)

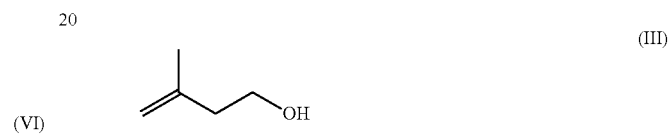
(III)

with an aldehyde of the formula (IV)

$R^1$—CHO (IV)

where $R^1$ in the formula (IV) has the meaning given above, in the presence of an acidic catalyst, wherein the reaction takes place in a reactor with at least one downstream separating column, where a part stream of the discharge from the first reactor is stripped off and returned to the reactor via an external circuit.

DESCRIPTION OF THE INVENTION

The process according to the invention has the following advantages:

The process according to the invention permits a lower thermal stressing of the reactor contents by virtue of a lower maximum temperature and/or the avoidance of temperature peaks.

The process thus permits higher yields and/or a higher selectivity with regard to the target compounds.

A lower maximum temperature and/or the avoidance of temperature peaks are also advantageous from a safety point of view and/or permit a longer catalyst service life.

Specifically the use of a catalyst fixed-bed can additionally have an advantageous effect on the catalyst service life. Consequently, laborious start-up and shut-down operations for exchanging spent catalyst and/or for regenerating the catalyst are avoided. Moreover, the use of a catalyst fixed-bed also reduces the mechanical stress and decomposition of the catalyst.

Unless stated more precisely below, the terms "2-substituted 4-hydroxy-4-methyltetrahydropyran" and "2-(2-methylpropyl)-4-hydroxy-4-methyltetrahydropyran" within the context of the invention mean cis/trans mixtures of any composition, and also the pure conformational isomers. The terms given above furthermore refer to all enantiomers in pure form, and to racemic and optically active mixtures of the enantiomers of these compounds.

Within the context of the present invention, the expression straight-chain or branched alkyl preferably stands for $C_1$-$C_6$-alkyl and particularly preferably for $C_1$-$C_4$-alkyl. Alkyl is in particular methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Specifically, alkyl is methyl, ethyl, n-propyl, isopropyl or isobutyl.

Within the context of the present invention, the expression straight-chain or branched alkoxy preferably stands for $C_1$-$C_6$-alkoxy and particularly preferably for $C_1$-$C_4$-alkoxy. Alkoxy is in particular methoxy, ethoxy, n-propyloxy, isopropyloxy, n-butyloxy, isobutyloxy, sec-butyloxy, tert-butyloxy, n-pentyloxy or n-hexyloxy. Specifically, alkoxy stands for methoxy, ethoxy, n-propyloxy, isopropyloxy or isobutyloxy.

Within the context of the present invention, the expression straight-chain or branched alkenyl preferably stands for $C_2$-$C_6$-alkenyl and particularly preferably for $C_2$-$C_4$-alkenyl. Besides single bonds, the alkenyl radical also has one or more, preferably 1 to 3, particularly preferably 1 or 2 and very particularly preferably one, ethylenic double bond. Alkenyl stands in particular for ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

Within the context of the invention, cycloalkyl refers to a cycloaliphatic radical having preferably 3 to 10, particularly preferably 5 to 8, carbon atoms. Examples of cycloalkyl groups are in particular cyclopropyl, cyclobutyl, cyclopentyl, cyclohexyl, cycloheptyl or cyclooctyl. Specifically, cycloalkyl is cyclohexyl.

Substituted cycloalkyl groups can have one or more (e.g. 1, 2, 3, 4 or 5) substituents depending on the ring size. These are preferably selected independently of one another from $C_1$-$C_6$-alkyl and $C_1$-$C_6$-alkoxy. In the case of a substitution, the cycloalkyl groups preferably carry one or more, for example one, two, three, four or five, $C_1$-$C_6$-alkyl groups. Examples of substituted cycloalkyl groups are in particular 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

Within the context of the present invention, the expression "aryl" comprises mono- or polynuclear aromatic hydrocarbon radicals having usually 6 to 18, preferably 6 to 14, particularly preferably 6 to 10, carbon atoms. Examples of aryl are in particular phenyl, naphthyl, indenyl, fluorenyl, anthracenyl, phenanthrenyl, naphthacenyl, chrysenyl, pyrenyl, etc., and specifically phenyl or naphthyl.

Substituted aryls can have one or more (e.g. 1, 2, 3, 4 or 5) substituents depending on the number and size of their ring systems. These are preferably selected independently of one another from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

One starting material for the process according to the invention is 3-methylbut-3-en-1-ol (isoprenol) of the formula (III),

Isoprenol is readily accessible on any scale by known methods from isobutene and formaldehyde and is commercially available. No particular requirements are placed on the purity, grade or preparation process of the isoprenol to be used according to the invention. It can be used in standard commercial grade and purity in the process according to the invention. Preference is given to using isoprenol which has a purity of 90% by weight or above, particularly preferably that with a purity of 95 to 100% by weight and very particularly preferably that with a purity of 97 to 99.9% by weight or even more preferably 98 to 99.8% by weight.

A further starting material for the process according to the invention is an aldehyde of the formula (IV) $R^1$—CHO, where $R^1$ in the formula (IV) has the meaning given above.

Preferably, $R^1$ in the compounds of the formulae (I), (II) and (IV) is a straight-chain or branched $C_1$-$C_{12}$-alkyl or straight-chain or branched $C_2$-$C_{12}$-alkenyl. Particularly preferably, $R^1$ is straight-chain or branched $C_1$-$C_6$-alkyl or straight-chain or branched $C_2$-$C_6$-alkenyl. In a further preferred embodiment, $R^1$ is phenyl.

Meanings of the radical $R^1$ that are preferred according to the invention are thus for example methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, very particularly preferably isobutyl (2-methylpropyl).

The radical $R^1$ is particularly preferably isobutyl or phenyl.

Aldehydes of the formula (IV) that are to be used with preference are: acetaldehyde, valeraldehyde, isovaleraldehyde, pentanal, hexanal, heptanal, benzaldehyde, citral, citronellal. According to the invention, aldehydes of the formula (IV) that are to be used with very particular preference are isovaleraldehyde and benzaldehyde, in particular isovaleraldehyde.

The reaction of the compounds (III) and (IV) takes place in an arrangement consisting of a reactor with at least one downstream separating column, i.e. the reactor and the separating column are connected in series. In one arrangement according to the invention, the individual reactor can also be replaced by two or more reactors connected in parallel. In a further embodiment, a plurality of separating columns can also be connected in parallel or in series.

A part stream of the discharge from the reactor is drawn off and returned to the reactor via an external circuit. This mode of operation is also referred to here and below as loop mode. The loop mode can additionally comprise backmixing internals and/or stirring devices in the reactor.

Preferably, the reaction takes place continuously. This means that all components connected in series, i.e. reactor and separating column(s), are each operated continuously.

In a suitable embodiment, the reaction takes place in the presence of a solvent. Optionally, for the purposes of carrying out the reaction according to the invention, the compounds of the formulae (III) and (IV), also referred to here and below as starting materials, are each supplied in the form of a mixture with a suitable solvent. Preferably, both starting materials (III) and (IV) are initially introduced in the same solvent. The solvent is preferably water or a solvent that is inert under the reaction conditions, such as, for example, tert-butyl methyl ether, cyclohexane, toluene, hexane or xylene. The specified solvents can be used on their own or in the form of mixtures. In a preferred embodiment, the reaction is carried out without the addition of an organic solvent. In a particularly preferred embodiment, the reaction takes place in the presence of water.

In a particularly preferred embodiment, heat is withdrawn from the part stream of the discharge from the reactor before it is returned to the reactor.

In a suitable embodiment, heat is additionally supplied to the discharge from the reactor before feeding it to the separating column. The stream division for the recirculation to the reactor will take place in this case before an interim cooling.

According to a further embodiment, at least one part stream is removed from the discharge from the top of the at least one separating column and returned to the reactor via an external recirculation. The top stream from the distillative separation, which consists essentially of the unreacted starting materials aldehyde, alcohol and water, can advantageously be returned to the reactor together with the pure starting material streams or separate therefrom.

In a preferred embodiment of the process according to the invention, the reaction in the reactor is carried out adiabatically.

Within the context of the present invention, the term "adiabatically" is understood in the technical sense and not in the physicochemical sense. Thus, the reaction mixture, upon flowing through the reactor, generally experiences a temperature increase on account of the exothermic reaction. Adiabatic reaction implementation is understood as meaning a procedure in which the amount of heat that is released during the reaction is absorbed by the reaction mixture in the reactor and no cooling takes place by means of cooling devices. Consequently, the heat of reaction is substantially removed from the reactor with the reaction mixture. It will be appreciated that a residual amount is released into the surroundings as a result of natural heat conduction and/or radiation from the reactor.

In an alternative embodiment of the process according to the invention, the reactor is operated largely isothermally.

Within the context of the present invention, "operated largely isothermally" is understood as meaning theta narrow temperature interval is observed in the respective reaction zone. If the reactor is "operated largely isothermally", then within the context of the present invention this should be understood as meaning that the temperature interval $\Delta T$ in the reactor is smaller than the adiabatic temperature increase. For the temperature interval in the reactor, preferably $\Delta T \leq 12$ K, particularly preferably $\Delta T \leq 10$ K.

For a largely isothermic operation of the reactor, heat transfer surfaces are suitably arranged in the inside of the reactor used, i.e. the reactor used comprises an internally arranged heat exchanger.

According to a particularly preferred embodiment, the reactor used is a fixed-bed reactor.

Preferably, the reaction takes place in the presence of an acidic catalyst which is selected from hydrochloric acid, sulfuric acid, methanesulfonic acid, p-toluenesulfonic acid and strongly acidic cation exchangers. In particular, the reaction is carried out in the presence of a strongly acidic cation exchanger.

Preferably, the alcohol of the formula (III) and the aldehyde of the formula (IV) are used in a molar ratio in the range from 0.7:1 to 2:1.

Preferably, the alcohol of the formula (III) and the aldehyde of the formula (IV) are reacted in the presence of at least 3% by weight, particularly preferably at least 5% by weight, of water. The alcohol of the formula (III) and the aldehyde of the formula (IV) are reacted for example in the presence of 3% by weight to 15% by weight of water, preferably from 5% by weight to 12% by weight. The percent by weight given above are based here on the amount of the reaction mixture, consisting of the components of the formulae (III) and (IV) and also water.

As a rule, the reaction of the alcohol of the formula (III) is carried out with the aldehyde of the formula (IV) in the presence of about at least 10 mol % of water, where the amount of water is based on the amount of the starting material optionally used in deficit, or in the case of an equimolar reaction on the quantitative amount of one of the two starting materials. Above the stated value, the amount of water can be chosen freely and is limited only by processing or cost aspects. Water can also be used in a large excess, for example in 10- to 100-fold excess, or even more. Preferably, a mixture is prepared from the alcohol of the formula (III) and the aldehyde of the formula (IV) with the selected amount of water, meaning that the added water remains dissolved in the mixture, i.e. a two-phase system is not present.

In a suitable embodiment, the starting materials are reacted in the presence of at least 25 mol %, preferably at least 50 mol %, of water. For example, the starting materials are reacted in the presence of 25 to 150 mol %, preferably from 40 to 150 mol %, particularly preferably from 50 to 140 mol %, in particular from 50 to 80 mol %, of water. Here, the amount of water used refers to the quantitative amount of the starting material optionally used in deficit or, in the case of an equimolar reaction, to the quantitative amount of one of the two.

In a suitable embodiment of the process according to the invention, the reaction is carried out at a temperature in the range from 0° C. to 70° C. preferably in the range from 20° C. to 70° C., particularly preferably in the range from 20° C. to 60° C.

In a likewise suitable embodiment of the process according to the invention, the reaction is carried out at a pressure in the range from 1 bar to 15 bar.

In a suitable embodiment, an additional thorough mixing can take place in the reactor used. An additional thorough mixing is advantageous particularly if the reaction takes place with long residence times of the reaction mixture. Both static and also dynamic mixing devices are suitable. Suitable mixing devices are sufficiently known to the person skilled in the art. For the purposes of thorough mixing, the feed streams can preferably be fed into the reactor by suitable mixing devices, such as nozzles.

The loop mode described above is particularly advantageously suitable for regulating the reaction temperature and the heat transfer between reaction medium, apparatus walls and surroundings. A further option for controlling the heat balance consists in regulating the entry temperature of the starting materials and/or of the recycle stream. Thus, a lower temperature of the entering feed generally leads to an improved dissipation of the heat of reaction. As the catalyst activity diminishes, the entry temperature chosen can be higher in order to achieve a higher rate of reaction and to thereby compensate for the diminishing catalyst activity. The service life of the catalyst used can thus be advantageously increased.

The recycle stream is generally returned to the reaction system chemically unchanged. If desired, the temperature and/or the pressure can be adjusted to the desired values prior to the recirculation. The recycle stream can be fed into the reactor together with one, two or three of the feed streams or separately therefrom. The quantitative weight ratio of the recycle stream fed into the reactor to the total feed stream is preferably in a range from 1:1 to 50:1, particularly preferably in a range from 2:1 to 30:1, in particular in the range from 5:1 to 20:1.

The top product, which consists essentially of the starting materials isovaleraldehyde and isoprenol and also water, is drawn off at the top of the separating column and can advantageously be returned to the reactor. The top product is generally returned to the reaction system chemically unchanged. If desired, the temperature and/or the pressure can be adjusted to the desired values prior to the recirculation. The top product can be returned to the reactor together with one, two or three of the feed streams or separately therefrom. As a result of the described recirculation of starting materials, the feed stream into the reactor can be reduced by the corresponding amount of starting materials.

Preferably, the reaction takes place in the presence of a strongly acidic cation exchanger. Here, the term strongly acidic cation exchanger is understood as meaning a cation exchanger in the $H^+$ form which has strongly acidic groups. The strongly acidic groups are generally sulfonic acid groups. The acidic groups are generally bonded to a polymer matrix, which may be e.g. gel-like or macroporous. A preferred embodiment of the process according to the invention is accordingly characterized in that a strongly acidic cation exchanger having sulfonic acid groups is used. Suitable strongly acidic cation exchangers are described in WO 2010/133473 and WO 2011/154330, to which reference is made here in its entirety.

Of suitability for the use are strongly acidic ion exchangers (such as e.g. Amberlyst™, Amberlite®, Dowex®, Lewatit®, Puralite®, Serdolit®), which are based on polystyrene and which comprise copolymers of styrene and divinylbenzene as carrier matrix with sulfonic acid groups in $H^+$ form, and also ion exchanger groups functionalized with sulfonic acid groups ($-SO_3H$). The ion exchangers differ in the structure of their polymer backbones, and a distinction is made between gel-like and macroporous resins. In a specific embodiment, a perfluorinated polymeric ion exchanger resin is used. Resins of this type are sold e.g. under the name Nafion® by DuPont. One example of such a perfluorinated polymeric ion exchanger resin which may be mentioned is Nafion® NR-50.

Commercially available strongly acidic cation exchangers suitable for the reaction are known for example under the trade names Lewatit® (Lanxess), Purolite® (The Purolite Company), Dowex® (Dow Chemical Company), Amberlite® (Rohm and Haas Company), Amberlyst™ (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nation® NR-50.

The strongly acidic on exchanger resins are generally regenerated with hydrochloric acid and/or sulfuric acid.

In a specific embodiment, the 3-methylbut-3-en-ol (III) and the aldehyde (IV) are reacted in the presence of a strongly acidic cation exchanger and in the presence of water. In principle, the reaction mixture can already comprise small amounts of water which can be released as a result of the dehydrogenation of the process product of the formula (I) as possible secondary reaction. According to a specific embodiment, water can also additionally be added to the reaction mixture as well as isoprenol (III) and the aldehyde of the formula (IV) and some water from the reaction.

Preferably, the alcohol of the formula (III) and the aldehyde of the formula (IV) are reacted in the presence of at least 3% by weight, particularly preferably at least 5% by weight, of water. The alcohol of the formula (III) and the aldehyde of the formula (IV) are reacted for example in the presence of 3% by weight to 15% by weight of water, preferably from 5% by weight to 12% by weight. The stated above percent by weight here are based on the total amount of the reaction mixture consisting of the components of the formulae (III) and (IV) and also water.

Above the stated value, the amount of water can be chosen freely and is limited, if at all, only by processing or cost aspects and it is entirely possible for it to be used in a large excess, for example in 5- to 15-fold excess or even more. Preferably, a mixture of isoprenol (III) and the aldehyde of the formula (IV), preferably isovaleraldehyde, is prepared with the amount of water to be added such that the added water remains dissolved in the mixture of isoprenol and the aldehyde, i.e. a two-phase system is not present.

Usually, within the context of this embodiment of the process according to the invention, the starting materials isoprenol (III) and the aldehyde of the formula (IV) are reacted in the presence of at least 25 mol %, preferably at least 50 mol %. For example, the starting materials are reacted in the presence of from 25 to 150 mol %, preferably from 40 to 150 mol %, particularly preferably from 50 to 140 mol %, in particular from 50 to 80 mol %, of water. In this connection, the amount of water used refers to the quantitative amount of the starting material optionally used in deficit or, in the case of an equimolar reaction, to the quantitative amount of one of the two.

For the reaction of isoprenol (III) with the aldehyde (IV), the stated starting materials and optionally the added water can be brought into contact with the acidic cation exchanger. Preferably, isoprenol (III), aldehyde (IV) and optionally the added water are used in the form of a mixture. The specified starting materials, i.e. isoprenol (III) and the aldehyde (IV) and the water to be used in the above amount can be brought into contact with one another and/or mixed in any desired order.

The amount of strongly acidic cation exchanger is not critical and can be chosen freely within wide limits taking into consideration the economic and processing aspect. The reaction can accordingly be carried out both in the presence of catalytic amounts and also in the presence of large excesses of the strongly acidic cation exchanger. The specified strongly acidic cation exchangers can be used either individually or in the form of mixtures.

The space velocity is for example in the range from 50 to 2500 mol per $m^3$ of catalyst and h, preferably in the range from 100 to 2000 mol per $m^3$ of catalyst and h, in particular in the range from 130 to 1700 mol per $m^3$ of catalyst and h, where the quantitative amount in mol refers to the starting material of the formula (IV).

The reaction in the presence of a strongly acidic cation exchanger can if desired also additionally be carried out in the presence of a solvent that is inert under the reaction conditions. Suitable solvents are, for example, tert-butyl methyl ether, cyclohexane, decalin, hexane, heptane, naphtha, petroleum ether, toluene or xylene. The specified solvents can be used on their own or in the form of mixtures with one another. Preferably, the reaction is carried out in the presence of a strongly acidic cation exchanger without the addition of an organic solvent.

Preferably, the reaction of isoprenol (III) with the selected aldehyde (IV) is carried out in the presence of water and in the presence of a strongly acidic cation exchanger at a temperature in the range from 0 to 70° C., particularly preferably at a temperature in the range from 20 to 70° C. and in particular at a temperature in the range from 20 to 60° C. This is the temperature of the reaction mixture.

The reaction mixture drawn off from the reactor is subjected to a distillative separation in a separating column downstream of the reactor. Suitable separating columns comprise distillation columns, such as tray columns, which may be equipped with bubble caps, sieve plates, sieve trays, packings, packing bodies, valves, side offtakes, etc., evaporators, such as thin-film evaporators, falling-film evaporators, forced-circulation evaporators, Sambay evaporators, etc. and combinations thereof.

The separating column can have separation-efficient internals, which are preferably selected from trays, structured packings, e.g. sheet-metal or fabric packings, such as Sulzer Mellapak®, Sulzer B X, Kühni Rombopak, Montz B1 or Montz A3, or random beds of packing bodies, such as e.g. Dixon rings, Raschig rings, high-flow rings or Raschig super rings. Structured packings, preferably sheet-metal or fabric packings, with a specific surface area of from 100 to 750 $m^2/m^3$, in particular 250 to 500 $m^2/m^3$, have proven to be particularly useful. They permit high separation efficiencies coupled with low pressure drops.

Preferably, for the separation, in a separating column is used which comprises
- a feed column with rectifying section positioned above the feed point, and stripping section positioned below the feed point,
- an upper combining column communicating with the upper end of the rectifying section, and a lower combining column communicating with the lower end of the stripping section, and
- a take-off column communicating with the upper combining column and the lower combining column.

Preferably, the separation takes place in the separating column by
  i. introducing the reaction product from the reactor into a feed column with rectifying section positioned above the feed point and stripping section positioned below the feed point,
  ii. providing an upper combining column communicating with the upper end of the rectifying section with condenser at the upper end of the column, and a lower combining column communicating with the lower end of the stripping column with heating device at the lower end of the column,
  iii. providing a take-off column communicating with the upper combining column and the lower combining column and having at least one side take-off,
  iv. drawing off from the take-off column at the top or in the upper region the compounds with a boiling point lower than the 2-substituted 4-hydroxy-4-methyltetrahydropyrans (I),
  v. drawing off as at least one side take-off at least some of the 2-substituted 4-hydroxy-4-methyltetrahydropyrans (I) and
  vi. drawing off at the bottom or in the lower region of the lower combining column the 2-substituted 4-hydroxy-4-methyltetrahydropyrans (I) that are not drawn off as side take-off, and the compounds with a higher boiling point than the 2-substituted 4-hydroxy-4-methyltetrahydropyrans (I).

In a preferred embodiment, the take-off removed from the take-off column at the top or in the upper region comprises essentially:
- unreacted 3-methylbut-3-en-1-ol of the formula (III),
- unreacted aldehyde of the formula (IV),
- small amounts or no 4-hydroxy-4-methyltetrahydropyrans of the formula (I),
- water.

The top product obtained in this way can optionally be subjected to a phase separation to separate off the majority of the water. Apart from such a phase separation, the top product obtained in this way can generally be returned to the reactor without further work-up. If desired, the top product can be subjected to a further work-up for separating off at least some of the components different from the starting materials (III) and (VI). For this purpose, the top product can be subjected e.g. to a further distillative separation.

In a preferred embodiment, one side stream is drawn off from the take-off column or two side streams are drawn off from the take-off column. In a specific embodiment, only one side stream is drawn off from the take-off column.

If two or more take-offs are removed from the separating column which comprise 2-substituted 4-hydroxy-4-methyltetrahydropyrans (I), e.g. two different side take-offs or one side take-off and one bottom take-off, then these generally differ with regard to the composition of the stereoisomers. Consequently, the isolation of a fraction enriched in cis-diastereomers compared with the reaction product removed from the reactor and of a fraction enriched in trans-diastereomers is possible. In the event of adequate separation efficiency of the separating column used, at least one of the diastereomers can, optionally, be obtained in pure form.

The feed column, take-off column, upper combining column and lower combining column can be discrete structural elements or be configured as a section or chamber of a distillation column which combines a number of functions. The expression "communicating columns" means that there is an exchange both of rising vapors and also of discharging condensate between them.

In one preferred embodiment of the process according to the invention, the distillative separation takes place in an arrangement of separating columns which comprises a dividing-wall column or an interconnection of at least two thermally coupled conventional distillation columns.

Dividing-wall columns are special distillation columns with at least one feed point and at least three removal points. Between evaporator and condenser is positioned the so-called rectification region in which some of the condensate formed in the condenser moves downwards in liquid form as runback countercurrently to the vapors rising from the evaporation apparatus. The rectification region comprises, in one part region of the column below and/or above the feed point, at least one separating device (dividing wall), acting in a longitudinal direction, to prevent crossmixing of the liquid stream and/or vapor stream, which facilitates distillative separation of substance mixtures. The basic principle of the dividing-wall columns has been known for a long time and is described for example in U.S. Pat. No. 2,471,134, in EP-A-0 122 367 or in G. Kaibel, Chem. Eng. Technol. Vol. 10, 1987, pages 92 to 98.

The general structure of a dividing-wall column comprises at least one side feed point on one side of the dividing wall and at least three removal points, at least one of which is on the other side of the dividing wall. Since in this type of construction, crossmixing of liquid stream and/or vapor stream is prevented in the region of the dividing wall, it is possible to obtain the side products in pure form. This generally reduces the number of distillation columns required overall for the separation of multicomponent mixtures. Moreover, capital costs and also energy can be saved when using dividing-wall columns compared with a simple serial arrangement of two conventional distillation columns (see M. Knott, Process Engineering, Vol. 2, 1993, February, pages 33 to 34).

Within the context of the invention, conventional distillation columns is the term used to refer to all distillation columns which do not comprise a dividing wall. In thermally coupled conventional distillation columns, mass and energy streams are mutually exchanged. Consequently, a significant saving of energy is possible compared to a simple serial arrangement of conventional distillation columns. As an alternative to the dividing-wall column, preference is given to an arrangement of two thermally coupled distillation columns. An overview of various arrangements is given for example in G. Kaibel et al., Chem.-Ing.-Tech., Vol. 61, 1989, pages 16 to 25 and G. Kaibel et al., Gas Separation & Purification, Vol. 4, 1990, June, pages 109 to 114.

In a first preferred embodiment, a distillation column with a thermally coupled precolumn is used for the distillation, i.e. the take-off column, the upper combining column and the lower combining column are designed as a single-section distillation column, and the feed column is designed as a precolumn to the distillation column. In a second preferred embodiment, a distillation column with a thermally coupled post-column is used, i.e. the feed column, the upper combining column and the lower combining column are designed as a single-section distillation column and the take-off column is designed as a post-column to the distillation column. Distillation columns with connected auxiliary columns are known and described e.g. in Chem. Eng. Res. Des., Part A. Trans IChemE, March 1992, pp. 118-132, "The design and optimisation of fully thermally coupled distillation columns".

It has proven to be favorable to remove at least some of the compounds with a lower boiling point than the 2-substituted 4-hydroxy-4-methyltetrahydropyrans (I) from the reaction mixture removed from the reactor prior to introducing it into the feed column. In one specific embodiment, therefore, an arrangement of distillation columns is used for the distillative separation of the reaction product from the reactor which comprises an upstream conventional distillation column and a downstream dividing-wall column or a downstream interconnection of two thermally coupled conventional distillation columns.

Preferably, for the distillative separation,
the reaction mixture from the reactor is subjected firstly to a separation in a conventional distillation column, where a first top product is obtained which is enriched in the compounds of the formulae (III) and (IV) and comprises essentially no compounds of the formula (I), and a first bottom product is obtained which is enriched in the compounds (III) and (IV) and comprises the majority of the compounds of the formula (I), and the first bottom product is subjected to a separation in a dividing-wall column or in an interconnection of two thermally coupled conventional distillation columns, where a second top product is obtained which comprises the compounds (III) and (IV) not present in the first top product, and also optionally small amounts of the compounds of the formula (I), a side stream is obtained which consists essentially of compounds of the formula (I), and a second bottom product is obtained which comprises the compounds of the formula (I) which are not present in the top product and are not present in the side stream.

The first top product comprises essentially no compounds of the formula (I). This means that the fraction of the compounds of the formula (I) in the first top product is at most 5% by weight, particularly preferably at most 2% by weight, especially at most 1% by weight, specifically at most 0.1% by weight, based on the total weight of the first top product. In a specific embodiment, the first top product comprises no compounds of the formula (I).

The second top product can comprise for example 0.1 to 25% by weight, particularly preferably 0.2 to 20% by weight, in particular 0.3 to 15% by weight, specifically 0.5 to 10% by weight, of compounds of the formula (I), based on the total weight of the second top product.

In a specific embodiment, the side stream consists only of compounds of the formula (I).

In a specific embodiment, the second bottom product consists only of compounds of the formula (I). Alternatively, the second bottom product can comprise compounds which have a higher boiling point than the compounds of the formula (I).

Preferably, according to this embodiment, the first top product (in particular the organic phase of the first top product depleted in water) and/or the second top product is returned to the reactor for the reaction. Here, it is unimportant if the second top product still comprises small amounts of the compounds of the formula (I) since these generally pass through the reaction in the reactor unchanged and can then optionally be separated off and put to good use.

As a rule, in this embodiment, the side product and the second bottom product are different with regard to the fraction of the stereoisomers of the compounds of the formula (I).

The work-up of the reaction product for obtaining the product of value can take place by customary methods known to the person skilled in the art. Preferably, the work-up of the reaction mixture comprises at least one distillation step. The reaction product can be separated in a known manner by distillation or rectification in order to thus obtain the product of value. For example, the work-up can take place analogously to the method described in WO 2011/154330, to which reference is made here in its entirety.

DESCRIPTION OF THE FIGURE

The process according to the invention is explained in more detail by reference to the FIGURE below without limiting it to this embodiment.

In FIG. 1 the following reference numerals are used:
1 Reactor
2 Cooling unit
5 Pump
8 Separating column
A Isoprenol
B Aldehyde
C Water D Recirculation stream
E Feed
F Top product
G Starting material The process according to the invention can be carried out with a reactor. The reactor can optionally be operated with interim cooling. Here, the reaction takes place in the back-mixed reactor system. In the back-mixed reactor, some or all of the circulation stream can be cooled. Division into two or more beds, optionally also with interim cooling, can likewise be realized in the one reactor.

After emerging from the reactor, at least one distillation stage follows. These can be operated in parallel or in series. Preferably, they are connected in series.

The FIGURE shows an embodiment of the process according to the invention with a reactor (1) and a separating column (8). The three starting materials isoprenol (A), aldehyde (B) and water (C) are introduced into the reactor (1) via three feeds. A discharge from the reactor (1) is removed via a line and the pump (5) and is divided into two part streams. A recirculation stream (D) is fed to the main reactor (1) via the cooling unit (2) together with the starting materials (A), (B) and (C). A feed (E) is passed to the separating column (8). The starting material (G) is removed as discharge at the bottom of the separating column (8) and optionally fed to a work-up stage. At the top of the separating column (8), the top product (F) is removed and returned at least in part to the reactor (1).

The reactor (1) is preferably configured as a fixed-bed reactor. In this connection, it is operated in loop mode, whereas the separating column (8) is operated in a straight pass. In the arrangement shown in the FIGURE, the reactor (1) and the separating column (8) are connected in series such that the temperature profile above the catalyst bed can be adjusted via the back-mixing in the reactor (1). As a result, a large temperature increase at the start of the reaction can be prevented.

The examples below serve to illustrate the invention without limiting it in any way.

EXAMPLES

Example 1 (Continuous Process with Partial Conversion and Recirculation)

An apparatus consisting of a reactor and a laboratory column was used. The reactor used was a jacketed reactor made of RA4 without heating medium for an adiabatic procedure with a length of 150 cm and an internal diameter of 2.6 cm.

The reactor was filled with 230 g (305 ml) of the cation exchanger. The cation exchanger was washed prior to use firstly several times with water, then once with methanol and finally with water so as to be methanol-free. The reactor was then conditioned by introducing a mixture of pyranol:water in a mass ratio of 95:5. The main reactor was then operated back-mixed with a recirculation stream of 2000 g/h, the recirculated stream being cooled to a temperature of 25° C. before reentering the main reactor. After conditioning the cation exchanger to the stated pyranol/water mixture, a mixture of isovaleraldehyde:isoprenol:water in a mass ratio of 45:50:5 was introduced at 25° C. and in a total quantitative stream of 100 g/h. This gave a crude product with a selectivity of 78.5% with regard to isovaleraldehyde with the following composition:
Isovaleraldehyde: 10.25 GC % by weight,
Isoprenol: 13.95 GC % by weight,
Dihydropyran isomers: 6.98 GC % by weight,
1,3-Dioxane: 3.18 GC % by weight,
Acetal: 0.63 GC % by weight,
trans-Pyranol: 14.60 GC % by weight,
cis-Pyranol: 40.07 GC % by weight,
Water: 6.8% by weight (according to Karl Fischer).

The reaction mixture was then subjected to the simultaneously running, continuous distillative separation, where the top product, consisting of isovaleraldehyde, isoprenol and water, was admixed with the feed of the main reactor and thereby returned. Simultaneously, the feed of the starting materials to the main stream was reduced by the corresponding amount.

The invention claimed is:

1. A process for the preparation of 2-substituted 4-hydroxy-4-methyltetrahydropyrans of the formula (I)

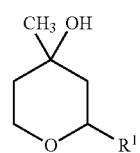

(I)

in which
R$^1$ is a straight-chain or branched C$_1$-C$_{12}$-alkyl, a straight-chain, or branched C$_2$-C$_{12}$-alkenyl, a cycloalkyl having in total 3 to 20 carbon atoms, optionally substituted with C$_1$-C$_{12}$-alkyl and/or C$_1$-C$_{12}$-alkoxy, or an aryl having in total 6 to 20 carbon atoms, optionally substituted with C$_1$-C$_{12}$-alkyl and/or C$_1$-C$_{12}$-alkoxy,
the process comprising a reaction of 3-methylbut-3-en-1-ol of the formula (III)

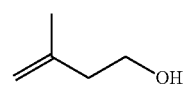

(III)

with an aldehyde of the formula (IV)

(IV)

where R$^1$ in the formula (IV) has the meaning above, in a reactor with at least one downstream separating column in the presence of an acidic catalyst, wherein a portion of a discharge stream from the reactor is returned to the reactor, and another portion of the discharge stream is directed to the separating column; wherein heat is removed from the portion of the discharge stream prior to returning to the reactor.

2. The process according to claim 1, wherein the reaction takes place continuously.

3. The process according to claim 1, wherein the reaction is conducted in the presence of a solvent.

4. The process according to claim 1, wherein heat is supplied to the portion of the discharge stream that is directed to the separating column.

5. The process according to claim 1, wherein at least one stream from the top of the at least one separating column is returned to the reactor.

6. The process according to claim 1, wherein the reaction is carried out adiabatically.

7. The process according to claim 1, wherein the reactor used is isothermal.

8. The process according to claim 7, wherein the reactor comprises an internally arranged heat exchanger.

9. The process according to claim 1, wherein the reactor is a fixed-bed reactor.

10. The process according to claim 1, wherein the radical R' is isobutyl or phenyl.

11. The process according to claim 1, wherein the acidic catalyst is selected from the group consisting of hydrochloric acid, sulfuric acid, methanesulfonic acid, p-toluenesulfonic acid and strongly acidic cation exchangers.

12. The process according to claim 1, wherein the acidic catalyst is a strongly acidic cation exchanger.

13. The process according to claim 1, wherein the alcohol of the formula (III) and the aldehyde of the formula (IV) are used in a molar ratio in the range from 0.7:1 to 2:1.

14. The process according to claim 1, wherein the reaction is conducted in the presence of 3% by weight to 15% by weight of water, based on the amount of the reaction mixture of components formulae (III) and (IV) and the water.

15. The process according to claim 1, wherein the reaction is carried out at a temperature in the range from 0° C. to 70° C.

16. The process according to claim 1, wherein the reaction is carried out at a pressure in the range from 1 bar to 15 bar.

17. A process for the preparation of 2-substituted 4-hydroxy-4-methyltetrahydropyrans of the formula (1)

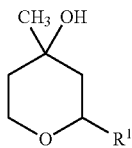

(I)

in which
R$^1$ is a straight-chain or branched C$_1$-C$_{12}$-alkyl, a straight-chain, or branched C$_2$-C$_{12}$-alkenyl, a cycloalkyl having in total 3 to 20 carbon atoms, optionally substituted with C$_1$-C$_{12}$-alkyl and/or C$_1$-C$_{12}$-alkoxy, or an aryl having in total 6 to 20 carbon atoms, optionally substituted with C$_1$-C$_{12}$-alkyl and/or C$_1$-C$_{12}$-alkoxy,
the process comprising reacting 3-methylbut-3-en-1-ol of the formula (III)

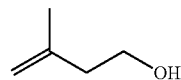

(III)

with an aldehyde of the formula (IV)

  (IV)

in a reactor, in the presence of an acidic catalyst, and the alcohol of the formula (III) and the aldehyde of the formula (IV) are present in a molar ratio in a range from 0.7:1 to 2:1, and the reaction is conducted in the presence of 3% by weight to 15% by weight of water, based on the amount of the reaction mixture of components formulae (III) and (IV) and the water, wherein a portion of a discharge stream from the reactor is recycled to the reactor, and another portion of the discharge stream is directed to at least one separating column;
wherein heat is removed from the portion of the discharge stream prior to returning to the reactor.

18. The process according to claim 17, wherein the reactor is a fixed-bed reactor, and the acidic catalyst is selected from the group consisting of hydrochloric acid, sulfuric acid, methanesulfonic acid, p-toluenesulfonic acid and strongly acidic cation exchangers.

19. The process according to claim 18, wherein the reaction is carried out at a temperature in the range from 20° C. to 70° C., and a pressure in the range from 1 bar to 15 bar, and R1 is selected from the group consisting of a straight-chain or branched C$_1$-C$_{12}$-alkyl, a straight-chain or branched C$_2$-C$_{12}$-alkyl, and phenyl.

* * * * *